(12) United States Patent
Chabrier de Lassauniere et al.

(10) Patent No.: US 6,297,281 B1
(45) Date of Patent: Oct. 2, 2001

(54) ASSOCIATION OF NO SYNTASE INHIBITORS WITH TRAPPERS OF OXYGEN REACTIVE FORMS

(75) Inventors: Pierre-Etienne Chabrier de Lassauniere, Paris; Dennis Bigg, Gif-sur-Yvette, both of (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 0 days.

(21) Appl. No.: 09/254,254
(22) PCT Filed: Sep. 5, 1997
(86) PCT No.: PCT/FR97/01567
   § 371 Date: Mar. 2, 1999
   § 102(e) Date: Mar. 2, 1999
(87) PCT Pub. No.: WO98/09653
   PCT Pub. Date: Mar. 12, 1998

(30) Foreign Application Priority Data

Sep. 6, 1996 (FR) .................................. 96 10875

(51) Int. Cl.[7] ............................. A01N 47/34; A01N 33/00
(52) U.S. Cl. ............................................. 514/589; 514/579
(58) Field of Search .......................... 424/94.4; 514/589, 514/579, 611; 588/416

(56) References Cited

PUBLICATIONS

Ohoi et al. : Involvement of Superoxide and Nitric Oxide In the Genesis of Reperfusion Arrhythmias in Rats: European J. of Pharm. 306, 123–31, 1996.*

Galley et al, Regulation . . . Antioxidants, Free Radical Biology & Medicine, vol. 21, No. 1 pp. 97–101, 1996.

* cited by examiner

*Primary Examiner*—Jon P. Weber
*Assistant Examiner*—Patricia Patten
(74) *Attorney, Agent, or Firm*—Bierman, Muserlian and Lucas

(57) ABSTRACT

The invention concerns a pharmaceutical composition containing, as active principle, at least one NO syntase inhibiting substance and at least one oxygen reactive form trapping substance, optionally with a pharmaceutically acceptable support. The invention also concerns a product containing at least one NO syntase inhibiting substance and at least one oxygen reactive form trapping substance as combined product of these active principles in separate form.

4 Claims, No Drawings

ASSOCIATION OF NO SYNTASE INHIBITORS WITH TRAPPERS OF OXYGEN REACTIVE FORMS

This application is a 371 of PCT/FR97/01567 filed Sep. 5, 1997.

The invention relates to a pharmaceutical composition comprising, as active ingredient, at least one substance inhibiting NO synthase and at least one substance trapping reactive forms of oxygen, and optionally a pharmaceutically acceptable carrier. The invention also relates to a product comprising at least one substance inhibiting NO synthase and at least one substance trapping reactive forms of oxygen as a combined product, in a separate form, of these active ingredients.

A pharmaceutical composition and a product according to the invention are advantageous in the treatment of pathological conditions where nitrogen monoxide and reactive forms of oxygen are involved, and particularly:

cardiovascular and cerebrovascular disorders including, for example, atherosclerosis, migraine, arterial hypertension, septic shock, cardiac or cerebral infarcts of ischaemic or haemorrhagic origin, ischaemia and thrombosis;

disorders of the central or peripheral nervous system such as, for example, neurodegenerative diseases including, in particular, cerebral infarct, senile dementia including Alzheimer's disease, Huntington's chorea, Parkinson's disease, Creutzfeld-Jakob disease, diseases due to prions, amyotrophic lateral sclerosis and also pain, cerebral trauma or trauma of the spinal cord, addiction to opiates, alcohol and habit-forming substances, erectile dysfunction and reproductive disorders, cognitive disorders, encephalopathy, depression, anxiety, schizophrenia, epilepsy, sleep disorders, eating disorders (anorexia, bulimia);

proliferative and inflammatory disorders such as, for example, atherosclerosis, pulmonary hypertension, glomerulonephritis, portal hypertension, psoriasis, osteoarthritis and rheumatoid arthritis, fibrosis, amyloidosis, inflammation of the gastrointestinal system (colitis, Crohn's disease) or of the pulmonary system and air passages (asthma, sinusitis);

diarrhoea, vomiting including that of autacoid origin, radioactive irradiation, solar radiation (UVA, UVB);

organ transplants;

autoimmune and viral diseases such as, for example, lupus, AIDS, parasitic and viral infections, diabetes, multiple sclerosis, myopathy;

cancer; and all pathological conditions characterised by the production or dysfunction of nitrogen monoxide and/or reactive forms of oxygen.

In all these pathological conditions, there is experimental evidence showing the involvement of nitrogen monoxide or reactive forms of oxygen (Kerwin et al., Nitric oxide: a new paradigm for second messengers, J. Med. Chem. 38, 4343–4362, 1995; Halliwell B., Gutteridge J M C., Free radicals in biology and medicine, 2nd ed., Oxford, Clarendon Press, 1989). This is the case, in particular, with the experimental cerebral infarct which illustrates the invention (Buisson et al., The neuroprotective effect of a nitric oxide inhibitor in a rat model of focal ischemia., Br J Pharmacol. 106, 766–767, 1992; Nowicki et al., Nitric oxide mediates neuronal cell death after focal cerebral ischemia in the mouse, Eur. J. Pharmacol. 204, 339–340, 1991; Zhao et al., Delayed treatment with the spin trap -phenyl-N-tert-butyl nitrone (PBN) reduces infarct size following transient middle cerebral artery occlusion in rats, Acta. Physiol. Scand., 1994; Schulz et al., Improved therapeutic window for treatment of histotoxic hypoxia with a free radical spin trap, J. Cereb. Blood Flow Metab. 15, 948–952 (1995)). In this context, the medicaments that can inhibit the formation of nitrogen monoxide or reactive forms of oxygen may bring beneficial effects. No combination of these two active ingredients, namely an NO synthase inhibitor and a trap of reactive forms of oxygen has been produced. As is set out in the experimental part, these two active ingredients act in a synergistic manner. In fact, these two active ingredients administered in subactive doses (i.e. doses which do not, by themselves, produce a therapeutic effect), produce a highly significant therapeutic effect when they are combined.

The advantage of this combination is to reduce considerably the doses of each of the active ingredients and thus to reduce considerably their undesirable effects whilst gaining therapeutic efficacy. This invention is illustrated particularly well in an experimental pathological model of neurodegeneration: cerebral ischaemia with reperfusion.

The invention provides, therefore, a pharmaceutical composition comprising, as active ingredient, at least one substance inhibiting NO syntase and at least one substance trapping reactive forms of oxygen, and optionally a pharmaceutically acceptable carrier.

More particularly, the invention provides a pharmaceutical composition comprising, as active ingredient, a substance inhibiting NO synthase and a substance trapping reactive forms of oxygen.

The term NO synthase inhibitor should be taken to mean any specific or non-specific inhibitor of one of the isoforms thereof whether it be constitutive (neuronal or endothelial) or inducible (Kerwin et al., Nitric oxide: a new paradigm for second messengers, J. Med. Chem. 38, 4343–4362, 1995).

The term trap of reactive forms of oxygen should be taken to mean any chemical or enzymatic substance capable of opposing or trapping the or one of the reactive forms of oxygen such as $O_2^-$, $OH^-$, $RO_2^-$, $RO \cdot$, $ONO_2^-$, $NO \cdot$, $NO_2 \cdot$ or $H_2O_2$ (Halliwell B., Gutteridge J M C., Free radicals in biology and medicine, 2nd ed., Oxford, Clarendon Press, 1989). These substances may be natural or synthetic and have antioxidant properties. (Santrucek and Krepelka, Antioxidants—Potential chemotherapeutic agents Drugs Future 13, 975–996, 1988; Jackson et al., Antioxidants: a biological defense mechanism for the prevention of atherosclerosis, Med. Res. Reviews 13, 161–182 (1993); Aruoma, Characterization of drugs as antioxidant prophylactics, Free Rad. Biol. Med. 20, 675–705 (1996)).

In a pharmaceutical composition according to the invention, the NO synthase inhibitor and the trap of reactive forms of oxygen may be in a separate form or a combined form forming a salt. Preferably, the salt is formed from a derivative of the substance inhibiting NO synthase containing at least one basic group, and from a derivative of the substance trapping reactive forms of oxygen containing at least one acid group. Thus, salts may be formed, according to methods known to the person skilled in the art, from NO synthase inhibitors such as, for example, amidines, guanidines, pyridines or piperidines as defined below, and traps of reactive forms of oxygen such as, for example, the phenolic acids as defined below, and more particularly 3,5-di-tert-butyl-4-hydroxybenzoic acid, caffeic acid, sinapic acid or gallic acid.

The invention also provides a product comprising at least one substance inhibiting NO synthase and at least one substance trapping reactive forms of oxygen as a combined product, in a separate form, for simultaneous or sequential use in the treatment of pathological conditions in which nitrogen monoxide and reactive forms of oxygen are involved such as cardiovascular and cerebrovascular disorders, disorders of the central or peripheral nervous system, proliferative and inflammatory diseases, organ transplants, autoimmune and viral diseases, cancer and all pathological conditions characterised by the production or dysfunction of nitrogen monoxide and/or reactive forms of oxygen.

In a pharmaceutical composition or a product according to the invention, the NO synthase inhibitor and the trap of reactive forms of oxygen may be in doses that may be identical or different. The dosages are chosen in terms of the compounds combined with suitable diluents or excipients.

The NO synthase inhibitor and the trap of reactive forms of oxygen may be administered simultaneously or sequentially by the same route of administration or by different routes, depending on whether they are in a separate or combined form. Preferably, the routes of administration are oral, parenteral or topical.

NO synthase inhibitors include compounds of the amino acid and non amino acid type. The amino acid type of NO synthase inhibitors may be compounds as described in the applications WO 95/00505, WO 94/12163, WO 96/06076 and EP 230037 incorporated by reference in the present application, or derivatives of L-arginine, ornithine or lysine as described in the applications WO 93/24126, WO 95/01972, WO 95/24382, WO 95/09619 and WO 95/22968, incorporated by reference in the present application.

The non amino acid type of NO synthase inhibitors may be compounds of the family comprising guanidines, isothioureas, nitro- or cyanoaryls, aminopyridines or aminopyrimidines, amidines, indazoles or imidazoles.

The guanidine NO synthase inhibitors may be the compounds as defined in the applications WO 95/28377, WO 91/04023, WO 94/21621, WO 96/18607 and WO 96/18608 incorporated by reference in the present application.

The isothiourea NO synthase inhibitors may be the compounds as defined in the applications WO 95/09619, WO 96/09286, WO 94/12165, WO 96/14842, WO 96/18607, WO 96/18608, WO 96/09286, EP 717040 and EP 718294 incorporated by reference in the present application.

The nitro- or cyanoaryl NO synthase inhibitors may be the compounds as described in the application WO 94/12163, incorporated by reference in the present application.

The aminopyridine or aminopyrimidine NO synthase inhibitors may be the compounds as defined in the applications WO 94/14780, WO 96/18616 and WO 96/18617 incorporated by reference in the present application.

The amidine NO synthase inhibitors may be the compounds as defined in the applications WO 95/11014, WO 96/01817, WO 95/05363, WO 95/11231, WO 96/14844 and WO 96/19440 incorporated by reference in the present application, or compounds such as N-phenyl-2-thiophenecarboxirrnidamide.

The indazole NO synthase inhibitors may be compounds corresponding to the general formula IA

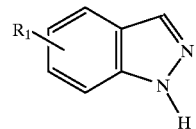

in which R1 represents one or more substituents chosen from the hydrogen atom, the nitro, halo, lower alkyl or lower alkoxy radical.

The imidazole NO synthase inhibitors may be compounds corresponding to general formula IIA

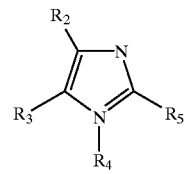

in which $R_2$ and $R_3$ represent, independently, the hydrogen atom, the halo, hydroxy, amino, alkyl or alkoxy radical, or $R_2$ and $R_3$ are joined together and form the phenyl radical condensed with the imidazole ring, the phenyl radical being optionally substituted by one or more substituents chosen from the hydroxy, trifluoromethyl, halo, carboxy, lower alkyl, lower alkoxy or lower alkylenyl radicals; $R_4$ represents a hydrogen atom, a lower alkyl, amino, lower alkyl amino or phenyl radical, the phenyl radical being optionally substituted by one or more substituents chosen from the hydroxy, trifluoromethyl, halo, carboxy, lower alkyl, lower alkoxy or lower alkenyl radicals; $R_5$ represents the hydrogen atom, a lower alkyl, amino, lower alkyl amino radical The traps of reactive forms of oxygen may be chosen from ascorbic acid, N-acetylcysteine, -carotene (Hao Chen et al., Free Radical Biology and Medicine 18 (5), 949–953 (1995)), the coenzyme Q10 (S. Tereao et al., J. Org. Chem., 44, 868 (1979)) or captodative compounds (H. G. Viehe et al., Acc. Res. 18, 148–154 (1985) incorporated by reference in the present application). The traps of reactive forms of oxygen may also be chosen from phenolic compounds, nitrones, derivatives of indole, imnidazoles or carbazoles, or they may be enzymes capable of neutralising the or one of the reactive forms of oxygen such as superoxide dismutase, catalase or glutathione peroxidase and mimetics thereof.

Phenolic compound traps of reactive forms of oxygen include probucol; ubiquinone; derivatives of tocopherol, namely α-, β-, γ-, ε-, τ- or δ-tocopherol or phenolic flavonoids (R. A. et al., Phytochemistry 27(4), 969–978 (1988), incorporated by reference in the present application). The phenolic compound traps of reactive forms of oxygen may also be chosen from compounds corresponding to general formula IB or IIB

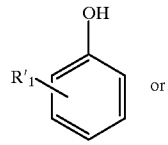
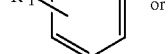

-continued

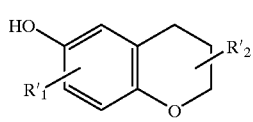

II_B in which R'₁ represents one or more substituents chosen from the hydrogen atom, the hydroxy, halo, carboxy, lower alkyl, lower alkoxy, lower alkenyl or alkoxy carbonyl radicals, the alkyl, alkoxy and alkenyl radicals optionally being substituted by a hydroxy, halo, carboxy or amino radical; and R'₂ represents one or more substituents chosen from the hydrogen atom or the optionally substituted lower alkyl radicals, lower alkoxy, hydroxy, halo, amino or carboxy radicals.

The nitrone traps of reactive forms of oxygen may be the compounds as defined in the applications WO 96/15110, WO 88/05044 and U.S. Pat. No. 5,310,916 incorporated by reference in the present application.

The indole derivative traps of reactive forms of oxygen may be compounds corresponding to general formula IIIB

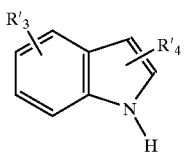

III_B in which R'₃ represents one or more substituents chosen from the hydrogen atom, the hydroxy, halo, lower alkyl or lower alkoxy radicals; R'₄ represents one or more substituents chosen from the hydrogen atom, the halo, hydroxy, amino, carboxy or alkylcarbonylaminoalkyl radicals.

The indole derivative traps of reactive forms of oxygen may also be compounds as defined in the application WO 96/26941.

The imidazole traps of reactive forms of oxygen may include preferably imidazole itself or cimetidine.

The carbazole traps of reactive forms of oxygen may include 4-hydroxycarbazole or carvedilol.

As used here, the term lower with reference to the alkyl and alkoxy groups designates saturated, linear or branched aliphatic hydrocarbon groups having 1 to 6 carbon atoms, such as, for example, methyl, ethyl, propyl, isopropyl, butyl, t-butyl, methoxy and ethoxy. With reference to the alkenyl groups, the term lower designates groups having 2 to 6 carbon atoms and one or more double or triple bonds such as, for example, the vinyl, allyl, propenyl, isopropenyl, pentenyl, butenyl, hexanyl, propenyl and butadienyl groups. The term halo means chloro, bromo, iodo or fluoro.

More particularly, the invention provides a composition or a product as defined above, characterised in that the NO synthase inhibitor is chosen from L-nitroarginine (LNA), the methyl ester of L-nitroarginine (LNAME), L-N-monomethylarginine (LNMMA), aminoguanidine, agmatine, 2-amino-1-(methylamnino) benzimidazole, 5-nitroindazole, 6-nitroindazole, 7-nitroindazole, 1,2-(trifluoromethylphenyl) imidazole (TRIM), 2-amino-4-methyl-6-(2-aminoethyl)pyridine, 2-iminopiperidine, 2-iminohomopiperidine, 2-imino-5,6-dihydro-1,3-thiazine, 2-imino-5,6-dihydro-1,3-oxazine, N-phenyl-2-thiophenecarboximidamide, 2-iminotetrahydropyrimidine, S-ethylisothiourea, S-methyl-L-thiocitrulline or S-ethyl-L-thiocitrulline; and the trap of reactive forms of oxygen is chosen from probucol, ubiquinone, α-, β-, γ-, ε-, τ- or δ-tocopherol, 3,5-di-tert-butyl-4-hydroxybenzoic acid, 2,3,6-trimethyl-2-hexyloxyphenol, 2,6-di-tert-butyl-4-methoxyplienol, eugenol, trolox, n-propyl gallate, tempole, caffeic acid, sinapic acid, gallic acid, 2,2,5,5-tetramethyl-3-pyrroline-1-oxyl-3-carboxylic acid, melatonin, 5-hydroxyindole-2-carboxylic acid, imidazole, cimetidine, ascorbic acid, N-aicetylcysteine, β-carotene, the coenzyme Q10, captodative compounds, 9-[2-(4-morpholinyl)ethyl]-2,4-di-1-pyrrolidinyl-9H-pyrimido[4,5-b]indole, 4-hydroxycarbazole or carvedilol.

The compounds which are NO synthase inhibitors and traps of reactive forms of oxygen are commercial products or may be prepared by methods known to the person skilled in the art (or by analogy to these latter) (P. Hamley et al, Bioorganic and medicinal chemistry letters, vol.5 (15), 1573–1576 (1995); W. M. Moore et al, J. Med. Chem., 39, 669–672 (1996); E. P. Garvey et al., The Journal of Biological Chemistry, vol. 269 (43), 26669–26676 (1994)).

The examples below are presented to illustrate the procedures above and should not be considered in any way as limiting the scope of the invention.

EXPERIMENTAL PART

Let A be the NO synthase inhibitor and B the trap of reactive forms of oxygen.

Example 1

Compound AB, a combination of the active ingredients A and B in the form of a salt in which A and B are in an equimolar quantity, with compound A: aminoguanidine, an inducible NO synthase inhibitor, and compound B: 3,5-di-tert-butyl-4-hydroxybenzoic acid, an antioxidant trap of free radicals containing oxygen.

Example 2

Compound AB, a combination of the active ingredients A and B in a separate form, with compound A: 7-nitroindazole, a constitutive NO synthase inhibitor of the neuronal type, and compound B: 3,5-di-tert-butyl-4-hydroxybenzoic acid, an antioxidant trap of free radicals containing oxygen.

Example 3

Compound AB, a combination of the active ingredients A and B in a separate form and administered by different routes, with compound A: NGnitroarginine, a powerful inhibitor of constitutive and inducible NO synthases, and compound B: 3,5-di-tert-butyl-4-hydroxybenzoic acid, an antioxidant trap of free radicals containing oxygen.

Pharmacological study of the products of the invention

The compounds of the invention underwent some biological tests in vitro and in vivo in order to prove their activity in blocking NO synthase (constitutive and inducible) and trapping free radicals. Their activity was evaluated on a model of focal cerebral ischaemia in the rat. In this model, which is regarded as a model of severe cerebral infarct approximating the clinical situation in man, excessive liberation of nitrogen monoxide and reactive forms of oxygen has been shown, as has the partially protective effect of NO synthase inhibitor or a trap of reactive forms of oxygen. The effects of the combination were compared with those produced by a treatment with the inhibitor of nitrogen monoxide or the trap of reactive forms of oxygen alone. The combination of an NO synthase inhibitor and of a trap of reactive forms of oxygen shows a highly significant protective effect on focal cerebral ischaemia whereas the effect of the NO synthase inhibitor or of the trap of reactive forms of oxygen taken separately and in the doses used is not significant. This proves the synergy between the NO synthase inhibitor and the trap of reactive forms of oxygen.

1) In vitro effect of constitutive NO synthase on the rat cerebellum

The test consists in measuring the conversion, by NO synthase, of L-arginine to L-citrulline. Samples of cerebella of Sprague-Dawley rats (300 g—Charles River) are taken rapidly, dissected at 4° C. and homogenised in a volume of extraction buffer (HEPES 50 mM, EDTA 1 mM, pH 7.4, pepstatin A 10 mg/ml, leupeptin 10 mg/ml) centrifuged at 21000 g for 15 min at 4° C. The assay is carried out in glass test tubes in which are distributed 100 l of incubation buffer containing 100 mM of HEPES, pH 7.4, 2 mM of EDTA, 2.5 mM of $CaCl_2$, 2 mM of dithiothreitol, 2 mM of reduced NADPH and 10 g/ml of calmodulin. 25 µl of a solution containing 100 nM of tritiated arginine (specific activity: 56.4 Ci/mmole, Amersham) and 40 µM of non radioactive arginine are added. The reaction is initiated by adding 50 µl of homogenised product, the final volume being 200 µl (the 25 µl shortfall being either water or the product being tested). After 15 min, the reaction is stopped with 2 ml of stop buffer (20 mM of HEPES, pH 5.5, 2 mM of EDTA). After passing samples over a column of 1 ml of DOWEX resin, the radioactivity is quantified by a liquid scintillation spectrometer.

The results are expressed in terms of the $IC_{50}$ value and are summarised in the table of paragraph 2 (first column of results entitled "constitutive NO synthase, formation of citrulline").

2) In vitro effect on inducible NO synthase of murine macrophages J774A1

Murine macrophages J774A1 produce a large quantity of nitrogen monoxide after activation by lipopolysaccharides (LPS) and interferon-γ(IFN-γ). The cells are cultivated in DMEM medium (Dulbecco's Modified Eagle Medium) enriched with 10% foetal calf serum at 37° C. under an atmosphere of 5% $CO_2$ after activation by LPS and IFN-γ. They are seeded in a quantity of 5000 cells/cm$^2$ in 150 cm$^2$ bottles. The incubations are carried out in the presence of LPS (1g/ml) and murine IFN-γ (50 U/ml) in DMEM enriched with 10% foetal calf serum. The NO synthase is isolated with an extraction buffer (HEPES 50 mM, pH 7.4, dithiothreitol 0.5 mM, pepstatin A 1 mg/ml, leupeptin 1 mg/ml, soya trypsin inhibitor 1 mg/ml, antipain 1 mg/ml, and PMSF 10 mg/ml). After sonication in the extraction buffer at 4° C., the homogenised products are ultracentrifuged (100,000 g with 3,5-di-tert.butyl-4-hydroxybenzoic acid 4° C. for 1 h). The protocol is then identical to that of cerebellum NO synthase except for the composition of the incubation buffer (100 mM of HEPES, pH 7.4, 1 mM dithiothreitol, 2.5 mM of $CaCl_2$, 10 M of tetrahydrobiopterin, FAD 10 µM, BSA 1 mg/ml, 2 mM of reduced NADPH). The results are expressed in terms of the $IC_{50}$ value and are summarised in the table of paragraph 2 (second column of results entitled "inducible NO synthase, formation of citrulline").

3) In vitro effect on the production of nitrites by murine macrophages J774A1

This test is used to measure the inhibitory activity of the products on inducible NO synthase of culture cells. The cells are cultivated in DMEM medium (Dulbecco's Modified Eagle Medium) enriched with 10% foetal calf serum at 37° C. under an atmosphere of 5% $CO_2$. For the experiments, they are distributed in 96-well plates (50,000 cells per well) and incubated in DMEM without phenol red containing 10% foetal calf serum with LPS (1 µg/ml) and murine IFN-γ(50 U/ml) in the presence or absence of the products to be tested. After 48 hours, the concentration of nitrites in the culture media, degradation products of nitrogen monoxide, is measured by a colorimetric method according to Green et al. (Analytical Biochemistry, 126, 131–138 (1982)). The results are expressed in terms of the $IC_{50}$ value and are summarised in the table of paragraph 2 (third column of results entitled "inducible NO synthase, formation of nitrites").

|  | $IC_{50}$ (µM) | | |
| --- | --- | --- | --- |
|  | Constitutive NO synthase (formation of citrulline) | Inducible NO synthase (formation of citrulline) | Inducible NO synthase (formation of nitrites) |
| Example 1 | | | |
| A | >300 | 29 | 22 |
| AB | >300 | 57 | 26 |
| Example 2 | | | |
| A | 0.9 | 25 | 51 |
| AB | 0.9 | 25 | 51 |

4) In vitro effect on the formation of superoxide anions

The activation of the macrophage cells J774A1 by phorbol myristate acetate (PMA) leads to the production of superoxide anions in a few minutes. These superoxide anions are able to oxidise a luminescent substrate, luminol. This reaction generates photons, the production of which is measured by means of a chemiluminometer. The effects of the products on the production of superoxide anions are tested by incubating the J774A1 cells at 37° C. in the presence of PMA, products to be tested, and luminol. The results are expressed in terms of the $IC_{50}$ value.

Example 1

| Product | $IC_{50}$ (µM) |
| --- | --- |
| A | inactive |
| B | 30 |
| AB | 30 |

5) Effect on focal cerebral ischaemia with reperfusion

The experiments are carried out on male Sprague-Dawley rats (Charles River) weighing between 330 and 360 g. After anaesthesia with isoflurane, the rats undergo transient occlusion of the middle cerebral artery described by Memezawa et al. (Exp. Brain Res. 89, 67–78, 1992). A wire is introduced into the anterior cerebral artery bringing about an occlusion of the middle cerebral artery. Two hours later, the wire is withdrawn so as to permit recirculation of the blood to the Willis polygon. The temperature of the animals is monitored and controlled for 6 hours after occlusion. Forty eight hours after occlusion, the rats are anlesthetised with isoflurane and decapitated. Samples of brain are taken rapidly and immersed for 2 minutes in isopentane at −15° C. Six sections 2 mm thick are obtained and placed in a solution containing 2% 2,3,5-triphenyltetrazolium chloride (TCC) for 20 min and then fixed with formalin. The infarcted zone appears white and the healthy zone red. The infarcted surface area is measured at the site of the (sections by means of an image analyser. The volume of the infarct is calculated by integrating these various surface areas in the knowledge that they are 2 mm apart. The products are administered intraperitoneally. The first treatment is carried out 4 hours after occlusion, that is, 2 hours after the w ire was withdrawn, then 24 hours afterwards.

Compound of example 1: 4 groups of animals are created:

Group 1: treated with physiol ogical serum
Group 2: treated with A (30 mg/kg)
Group 3: treated with B (20 mg/kg)
Group 4: treated with AB (50 mg/kg)

| No. of group | Volume of infarct | | % Protection |
|---|---|---|---|
| 1 | 270.4 ± 30.05 | — | |
| 2 | 233 ± 30.15 | NS | 13.8 |
| 3 | 250.9 ± 37.86 | NS | 7.1 |
| 4 | 89.6 ± 22.42 | ** | 63.2 |

(NS: result not significant; **: result very significant)

Compound of example 2: 4 groups of animals are created:
Group 1: treated with physiological serum
Group 2: treated with A (10 mg/kg)
Group 3: treated with B (20 mg/kg)
Group 4: treated with AB (A: 10 mg/kg and B: 20 mg/kg)

| No. of group | Volume of infarct | | % Protection |
|---|---|---|---|
| 1 | 270.4 ± 30.05 | — | |
| 2 | 238.9 ± 27.08 | NS | 11.7 |
| 3 | 250.9 ± 37.86 | NS | 7.1 |
| 4 | 69.6 ± 37.86 | ** | 74.3 |

(NS: result not significant; **: result very significant)

Compound of example 3: 4 groups of animals are created:
Group 1: treated with physiological serum
Group 2: treated with A (0.03 mg/kg i.v.)
Group 3: treated with B (20 mg/kg i.p.)
Group 4: treated with AB (A: 0.03 mg/kg i.v. and B: 20 mg/kg i.p.)

| No. of group | Volume of infarct | | % Protection |
|---|---|---|---|
| 1 | 237.68 ± 31.51 | | — |
| 2 | 238.14 ± 35.94 | NS | 0 |
| 3 | 222.9 ± 7.34 | NS | 6.2 |
| 4 | 136.5 ± 33.02 | ** | 42.6 |

(NS: result not significant; **: result very significant)

The results show that 3,5-di-tert-butyl-4-hydroxybenzoic acid used as a trap of reactive forms of oxygen in the dose of 20 mg/kg is inactive for protecting the animal from ischaemic attacks, and that aminoguanidine (NO synthase inhibitor) has low activity. On the other hand, the combination of the two compounds protects the animals from ischaemia in a highly significant manner.

Similarly, 7-nitroindazole used as an inhibitor of the constitutive form of NO synthase is not significantly active in the dose of 10 mg/kg; on the other hand, when combined with 3,5-di-tert-butyl-4-hydroxybenzoic acid, a highly significant protection is observed. This protective effect shows a synergy between the two active ingredients.

Similarly, the nitroarginine used as an NO synthase inhibitor and injected is not significantly active in the dose of 0.03 mg/kg. On the other hand, when it is combined with an intraperitoneal administration of 3,5-di-tert-butyl-4-hydroxybenzoic acid, a highly significant protection is observed. This protective effect shows that the synergy between the two active ingredients is also observed when the active ingredients are administered by different routes.

What is claimed is:

1. A pharmaceutical composition comprising at least one substance inhibiting NO synthase selected from the group consisting of aminoguanidine, nitroarginine and nitroimidazole, and 3,5-ditert-butyl-4-hydroxy-benzoic acid which traps reactive forms of oxygen.

2. A composition of claim 1 wherein substance inhibiting NO synthase is nitroarginine.

3. A composition of claim 1 wherein substance inhibiting NO synthase is aminoguamidine.

4. A composition of claim 1 wherein substance inhibiting NO synthase is nitroimidazole.

* * * * *